(12) United States Patent
Zierenberg et al.

(10) Patent No.: US 7,849,851 B2
(45) Date of Patent: Dec. 14, 2010

(54) NEBULIZER

(75) Inventors: Bernd Zierenberg, Bingen (DE); Klaus Noehl, Ingelheim (DE); Johannes Geser, Ingelheim (DE); Gilbert Wuttke, Dortmund (DE); Stefan Kaulmann, Ludwigsburg (DE); Hubert Kunze, Dortmund (DE); Andreas Fiol, Norderstedt (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 225 days.

(21) Appl. No.: 11/064,585

(22) Filed: Feb. 24, 2005

(65) Prior Publication Data

US 2005/0247305 A1  Nov. 10, 2005

(30) Foreign Application Priority Data

Feb. 24, 2004 (DE) .................. 10 2004 009 435

(51) Int. Cl.
*A61M 11/00* (2006.01)
*A61M 15/08* (2006.01)
*A62B 9/02* (2006.01)
*A01G 27/00* (2006.01)
*B67D 7/08* (2006.01)
*B67D 7/56* (2006.01)
*B67D 7/22* (2006.01)

(52) U.S. Cl. .................. 128/200.14; 128/200.22; 128/200.16; 128/200.23; 128/200.21; 128/205.24; 128/203.22; 128/203.23; 239/70; 239/71; 239/72; 239/73; 239/74; 222/41; 222/42; 222/43; 222/44; 222/45; 222/46; 222/47; 222/48; 222/49; 222/50

(58) Field of Classification Search ............ 128/200.22, 128/200.16, 200.23, 200.21, 205.24, 203.22, 128/203.23; 239/70–74; 222/41–50
See application file for complete search history.

(56) References Cited

U.S. PATENT DOCUMENTS

| 5,020,527 | A | * | 6/1991 | Dessertine | ............. | 128/200.23 |
| 5,209,375 | A | | 5/1993 | Fuchs | | |
| 5,284,133 | A | * | 2/1994 | Burns et al. | ............ | 128/200.23 |
| 5,363,842 | A | | 11/1994 | Mishelevich et al. | | |
| 5,392,768 | A | * | 2/1995 | Johansson et al. | ....... | 128/200.14 |
| 5,482,030 | A | | 1/1996 | Klein | | |
| 5,544,647 | A | | 8/1996 | Jewett et al. | | |
| 5,551,416 | A | * | 9/1996 | Stimpson et al. | ....... | 128/200.16 |
| 5,622,163 | A | | 4/1997 | Jewett et al. | | |

(Continued)

FOREIGN PATENT DOCUMENTS

DE  10061723 C2  7/2002

(Continued)

*Primary Examiner*—Patricia M Bianco
*Assistant Examiner*—Nihir Patel
(74) *Attorney, Agent, or Firm*—Roberts Mlotkowski Safran & Cole, P.C.

(57) ABSTRACT

A nebulizer having an insertable container and a monitoring device for counting actuations of the nebulizer is proposed. The monitoring device is mounted in a detachable housing part and directly detects movements of container during a nebulizing process, an air supply current in the region of a mouthpiece, and/or the production of aerosol, in order to detect this as the actual dispensing of fluid and actuation of the nebulizer, while preferably the time of actuation of the nebulizer is additionally detected and stored. This allows better monitoring and guidance for the user.

5 Claims, 6 Drawing Sheets

U.S. PATENT DOCUMENTS

| | | | |
|---|---|---|---|
| 5,957,124 A * | 9/1999 | Lloyd et al. | 128/200.22 |
| 5,964,416 A | 10/1999 | Jaeger et al. | |
| 6,149,054 A | 11/2000 | Cirrillo et al. | |
| 6,234,366 B1 | 5/2001 | Fuchs | |
| 6,237,589 B1 * | 5/2001 | Denyer et al. | 128/200.21 |
| 6,453,795 B1 | 9/2002 | Eicher et al. | |
| 6,510,847 B1 | 1/2003 | Helgesson et al. | |
| 6,578,741 B2 | 6/2003 | Ritsche et al. | |
| 6,595,389 B2 | 7/2003 | Fuchs | |
| 6,651,844 B2 | 11/2003 | Tomaka et al. | |
| 6,745,761 B2 * | 6/2004 | Christrup et al. | 128/200.14 |
| 2003/0078551 A1 | 4/2003 | Hochrainer et al. | |
| 2004/0010239 A1 | 1/2004 | Hochrainer et al. | |
| 2004/0065326 A1 | 4/2004 | MacMichael et al. | |
| 2005/0174216 A1 | 8/2005 | Lintell | |
| 2005/0177275 A1 | 8/2005 | Harvey et al. | |

FOREIGN PATENT DOCUMENTS

| | | |
|---|---|---|
| DE | 10225470 A1 | 12/2003 |
| EP | 0775499 B1 | 5/2003 |
| JP | 6-26891 U | 4/1994 |
| WO | 9114468 A1 | 10/1991 |
| WO | 9712687 A1 | 4/1997 |

* cited by examiner

NEBULIZER

BACKGROUND OF THE INVENTION

1. Field of the Invention

The present invention relates to a nebulizer according to the preamble of claim 1.

2. Description of the Prior Art

The starting point for the present invention is a nebulizer in the form of an inhaler, as shown, in principle, in WO 91/14468 and specifically in FIGS. 6a and 6b in WO 97/12687, and in FIGS. 1 and 2 of the present application. The nebulizer comprises, as a reservoir for a fluid that is to be nebulized, an insertable container with the fluid and a pressure generator with a drive spring for conveying and atomizing the fluid. By rotating an actuating member in the form of a lower housing part of the nebulizer the drive spring can be put under tension and fluid can be drawn up into a pressure chamber of the pressure generator. After manual actuation of a locking element, the fluid in the pressure chamber is put under pressure by the drive spring and nebulized, i.e., expelled to form an aerosol. During the tensioning process, on the one hand, and subsequent atomizing, on the other hand, the container performs a lifting movement. The nebulizer comprises a mechanical monitoring device that detects the rotation of the actuating member in order to count the actuations of the nebulizer. The known nebulizer operates exclusively mechanically, i.e., without propellant gas and without electricity. WO 91/14468 and WO 97/12687 are hereby incorporated by reference in their entireties. Generally, the disclosures thereof refer to a nebulizer having a spring pressure of 5 to 60 MPa, preferably 10 to 50 Mpa, on the fluid with volumes per actuation of 10 to 50 µl, preferably 10 to 20 µl, most preferably about 15 µl, per actuation and particle sizes of up to 20 µm, preferably 3 to 10 µm. Moreover, the disclosures therein preferably relate to a nebulizer with a cylinder-like shape that is about 9 cm to about 15 cm long and about 2 to about 5 cm wide and a nozzle spray spread of from 20° to 160°, preferably from 80° to 100°. These magnitudes also apply to the nebulizer according to the teaching of the invention as particularly preferred values.

A device is also known for detecting the actuation of a dispenser, wherein an expulsion conveyor is actuated by a lifting movement between an actuating member and a media container and in the actuating member is arranged a switch for detecting an actuation and producing an electrical counting signal (DE 100 65 160). During the linear lifting movement, the switch is not actuated directly by the container, but by a fixing screw of the device, so that, even when the container is not inserted, a counting signal is generated on each actuation.

DE 100 61 723 discloses a mechanical counter for counting metered releases of products in the form of liquids, pastes, or solids, particularly medicaments, from a supply container, particularly an aerosol container. Preferably, linear movement of the aerosol is counted.

Also known is a dispensing control for a media dispenser (DE 198 07 921 A1). This control comprises a store and an intermittent circuit that allows possible actuation only at certain times and blocks it at other times. The store can be programmed using a computer so that the barrier is only opened at certain times, for which purpose a program comprises a time switch component. A display tells the user when a dose is to be administered and when it is not. The store can detect the administration, after which it can be displayed on a screen using a computer at any time. In order to program and interrogate the memory or to charge up an energy store, the control may have an electrical connection for a suitable plug that is accessible from outside.

SUMMARY OF THE INVENTION

The aim of the present invention is to provide a nebulizer of the kind described above having an improved monitoring device, particularly allowing improved safety in use and possibly providing more information for the user and/or user monitoring.

This objective is achieved by a nebulizer according to claim 1. Advantageous features are recited in the subsidiary claims.

According to a first aspect of the present invention, the monitoring device is mounted on a detachable housing part of the nebulizer, particularly fixedly connected thereto, preferably cast therein. This allows the monitoring device, together with the housing part, to be removed easily from the nebulizer so that the monitoring device can very easily be switched on, programmed, started up, and/or read off, separately or independently of the nebulizer, and/or so that the entire monitoring device, together with the housing part, can be changed or a nebulizer can be fitted with a monitoring device if the housing part is compatible.

Another aspect of the present invention, which can also be realized independently, consists of detecting the actual dispensing of fluid and, in particular, counting it electronically as an actuation of the nebulizer. This results in improved monitoring and better safety of use and guidance for the user.

Actual dispensing is preferably detected by directly detecting movement, preferably actuation, of the container by means of a receiving sensor detecting an air supply current produced by inhalation and/or a spray sensor detecting the production of nebulized fluid or aerosol, particularly in the region of a mouthpiece. Accordingly, it is possible to determine with substantially greater certainty whether the dispensing of fluid has actually taken place or inhalation as actually occurred. Preferably, the monitoring is carried out not only qualitatively, but also quantitatively.

According to an alternative embodiment, the monitoring device detects and, in particular, records, by means of the receiving sensor, sufficiently strong and/or long lasting inhalation of the fluid nebulized by the nebulizer, and/or counts it as a (successful) actuation of the nebulizer or intake of fluid. This contributes to safer operation and improved monitoring.

Most preferably, the monitoring device of the nebulizer is provided with a timer and a memory so that the number and time of the actuations of the nebulizer can be detected and recorded, and/or repeated actuation within a given minimum period can be blocked, and/or so that a reminder signal preferably for a repeat application can be emitted or displayed, preferably after a given maximum period has elapsed.

When the number and times of the actual dispensing of fluid are detected and recorded, continuous monitoring is possible, e.g., by the doctor or in clinical trials. By consulting the monitoring device or memory, it is thus possible to detect when the liquid was administered and possibly what quantities were dispensed by the nebulizer.

Blocking of repeated actuation of the nebulizer within a predetermined, preferably adjustable and recordable minimum period, can prevent overdosing of the fluid, which is preferably a highly effective pharmaceutical composition.

By emitting a reminder signal, preferably for repeat actuation of the nebulizer after a predetermined, preferably adjustable and recordable maximum period has expired, a user can be reminded that a fresh inhalation is required. Thus, regular inhalation, i.e., administration of the fluid, can be assisted. In particular, the reminder signal can indicate the time until the next inhalation or actuation, or possibly overdue inhalation or actuation. The reminder signal is most preferably a warning or alarm signal, particularly as disclosed in WO 03/092576, the entirety of which are hereby incorporated by reference.

DESCRIPTION OF THE DRAWINGS

Further advantages, features, properties, and aspects of the present invention will become apparent from the following description of preferred embodiments referring to the drawings, wherein.

In the Figures, identical reference numerals are used for identical or similar parts, and corresponding or comparable properties and advantages are achieved even if the description is not repeated.

DESCRIPTION OF THE INVENTION

Figure 1:
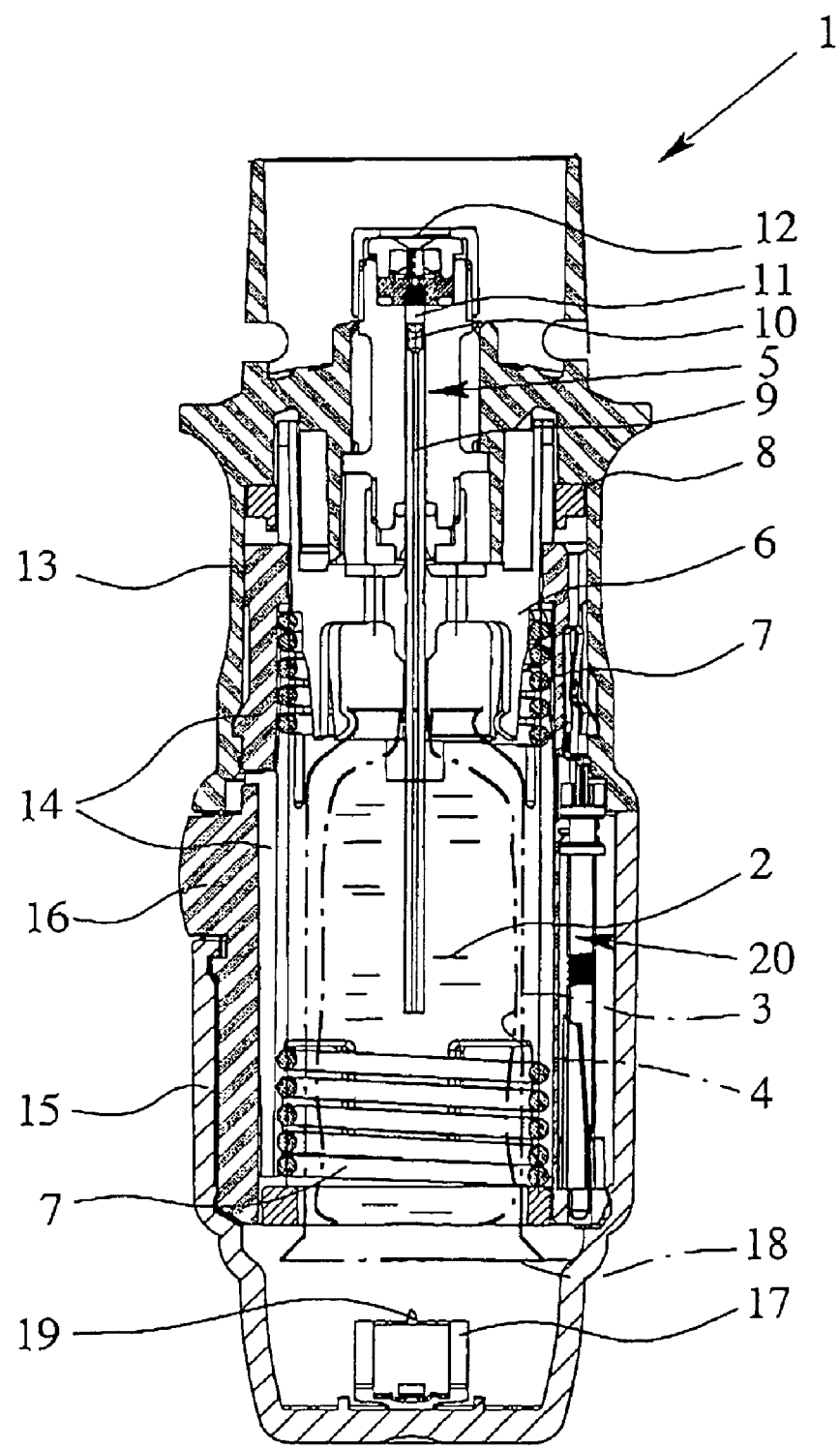
FIG. 1 is a diagrammatic section through a known nebulizer in the untensioned state.
Figure 2:
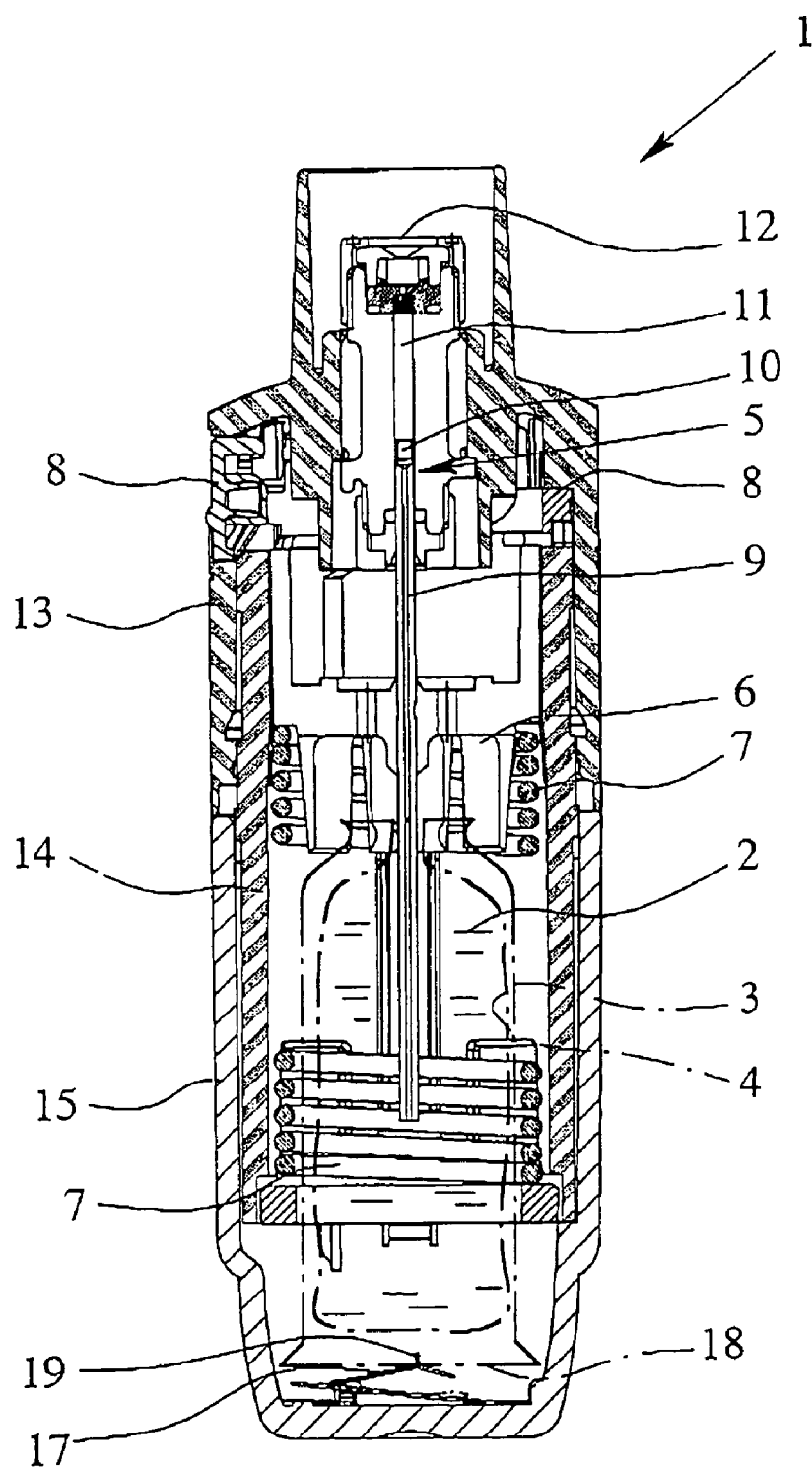
FIG. 2 shows a diagrammatic section through the known nebulizer in the tensioned state, rotated through 90° compared with FIG. 1.

FIGS. 1 and 2 show a known nebulizer 1 for nebulizing a fluid 2, particularly a highly effective pharmaceutical composition or the like, viewed diagrammatically in the untensioned state (FIG. 1) and in the tensioned state (FIG. 2). The nebulizer is constructed in particular as a portable inhaler and preferably operates without propellant gas.

When the fluid 2, preferably a liquid, more particularly a pharmaceutical composition, is nebulized, an aerosol is formed that can be breathed in or inhaled by a user (not shown). Usually the inhaling is done at least once a day, more particularly several times a day, preferably at set intervals.

The nebulizer 1 has an insertable and preferably exchangeable container 3 containing the fluid 2, which forms a reservoir for the fluid 2 that is to be nebulized. Preferably, the container 3 contains an amount of fluid 2 sufficient for multiple use, particularly for a given period of administration, such as one month, or for at least 50, preferably at least 100, doses or sprays.

The container 3 is substantially cylindrical or cartridge-shaped and, once the nebulizer 1 has been opened, the container can be inserted therein from below and changed if desired. It is preferably of rigid construction, the fluid 2, in particular, being held in a bag 4 in the container 3.

The nebulizer 1 has a pressure generator 5 for conveying and nebulizing the fluid 2, particularly in a preset and optionally adjustable dosage amount. The pressure generator 5 has a holder 6 for the container 3, an associated drive spring 7 with a locking element 8 that can be manually operated to release it, a conveying tube 9 with a non-return valve 10, a pressure chamber 11, and an expulsion nozzle 12.

As the drive spring 7 is axially tensioned, the holder 6 with the container 3 and the conveying tube 9 are moved downwards in the drawings, and fluid 2 is sucked out of the container 3 into the pressure chamber 11 of the pressure generator 5 through the non-return valve 10. As the expulsion nozzle 12 has a very small cross section of flow and is constructed, in particular, as a capillary, such a strong throttle action is produced that the intake of air by suction is reliably prevented at this point even without a non-return valve.

During the subsequent relaxation, after actuation of the locking element 8, the fluid 2 in the pressure chamber 11 is put under pressure by the drive spring 7 moving the conveying tube 9 back upwards, i.e., by spring force, and is expelled through the expulsion nozzle 12 where it is nebulized, particularly in particles in the µm or nm range, preferably particles destined for the lungs measuring about 5 µm. The conveying and nebulizing of the fluid 2 are thus carried out purely mechanically, in particular, without propellant gas and without electricity.

The nebulizer 1 comprises an upper housing part 13 and an inner part 14 which is rotatable relative thereto, on which an actuating member 15 is releasably fixed, particularly fitted on, preferably by means of a retaining element 16. In order to insert and/or replace the container 3, the actuating member 15 can be detached from the nebulizer 1.

By manually rotating the actuating member 15, the inner part 16 can be rotated relative to the upper housing part 13, as a result of which the drive spring 7 can be tensioned in the axial direction by means of a gear (not shown) acting on the holder 6. During tensioning, the container 3 is moved axially downwards until the container 3 assumes an end position as shown in FIG. 2 in the tensioned state. During the nebulizing process, the container 3 is moved back into its original position by the drive spring 7. The axial movement of the container 3 during actuation of the nebulizer 1 is hereinafter referred to as the stroke of the container 3.

The housing part 15 preferably forms a cap-like lower housing part and fits around or over a lower free end portion of the container 3. As the drive spring 7 is tensioned, the container 3 moves with its end portion (further) into the actuating member 15 or towards the end face thereof, while an axially acting spring 17 arranged in the actuating member 15 comes to bear on the base 18 of the container, and pierces the container 3 with a piercing element 19, when the container makes contact with it for the first time, to allow air in.

The nebulizer 1 comprises a monitoring device 20 that counts the actuations of the nebulizer 1 by detecting any rotation of the inner part 14 relative to the upper part 13 of the housing. The monitoring device 20 operates purely mechanically.

Figure 3:
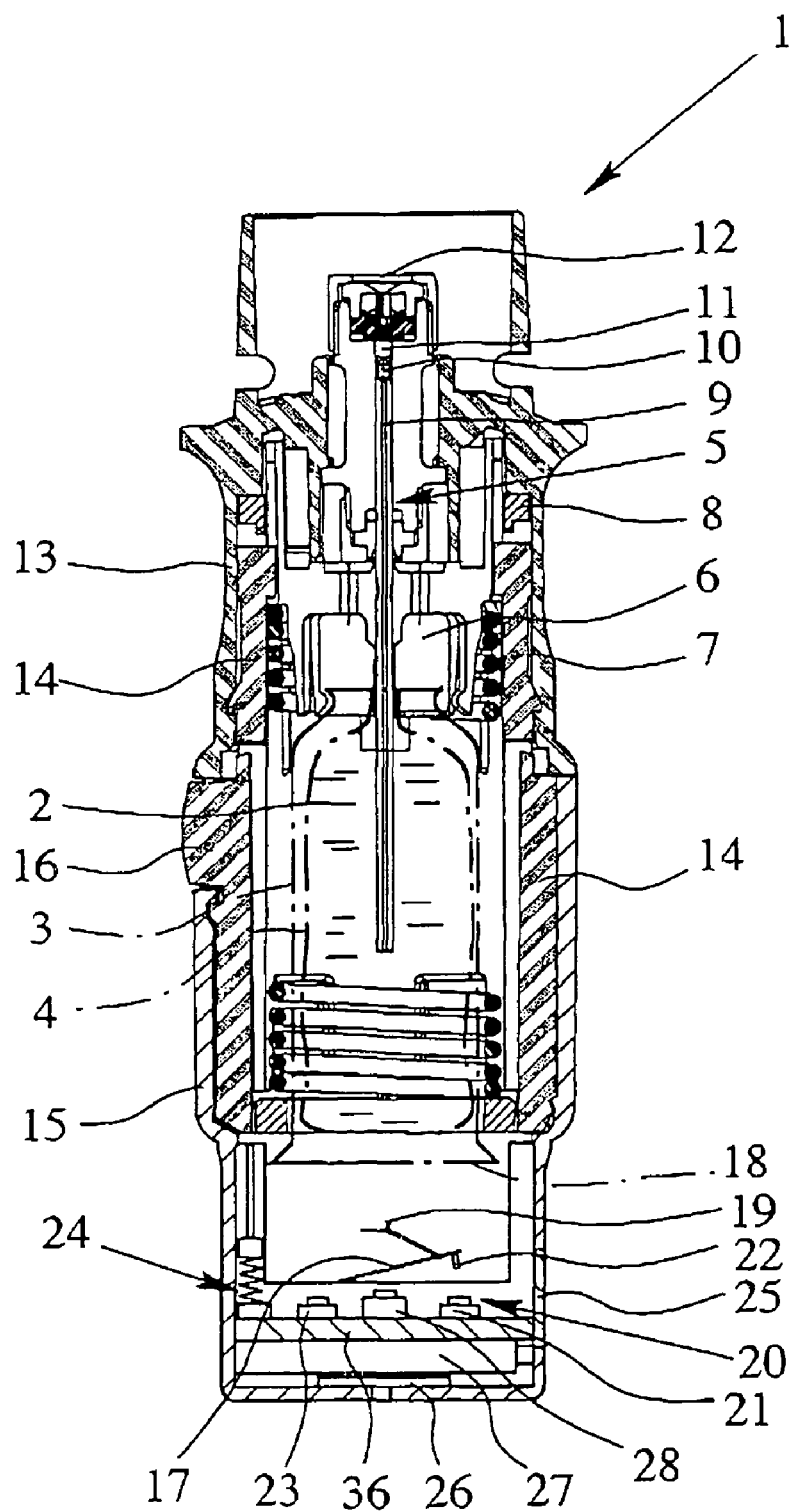
FIG. 3 is a diagrammatic sectional view of a lower housing part of a proposed nebulizer with integral monitoring device.
Figure 4:
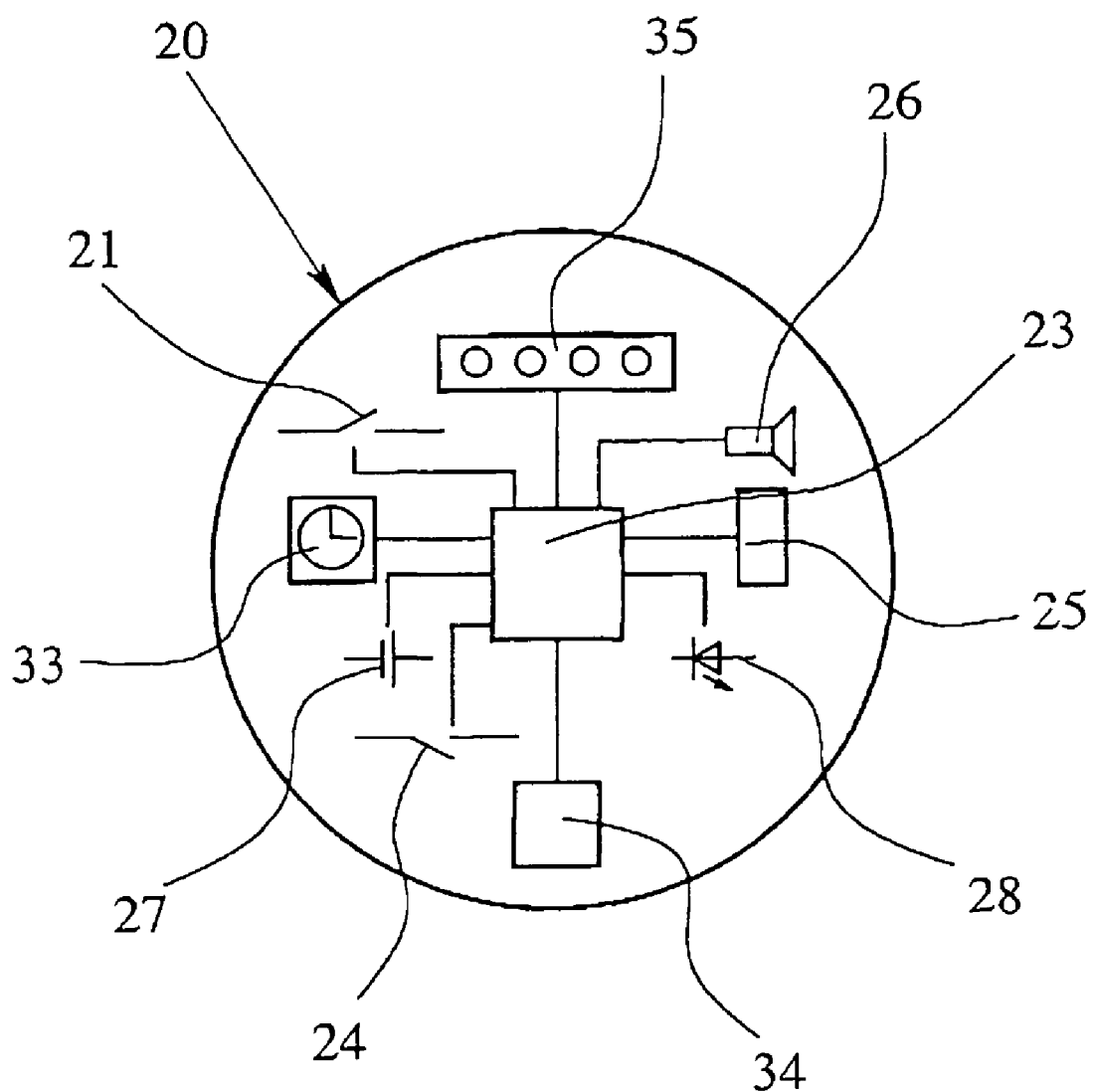
FIG. 4 is a block circuit diagram of the monitoring device.
Figure 5:
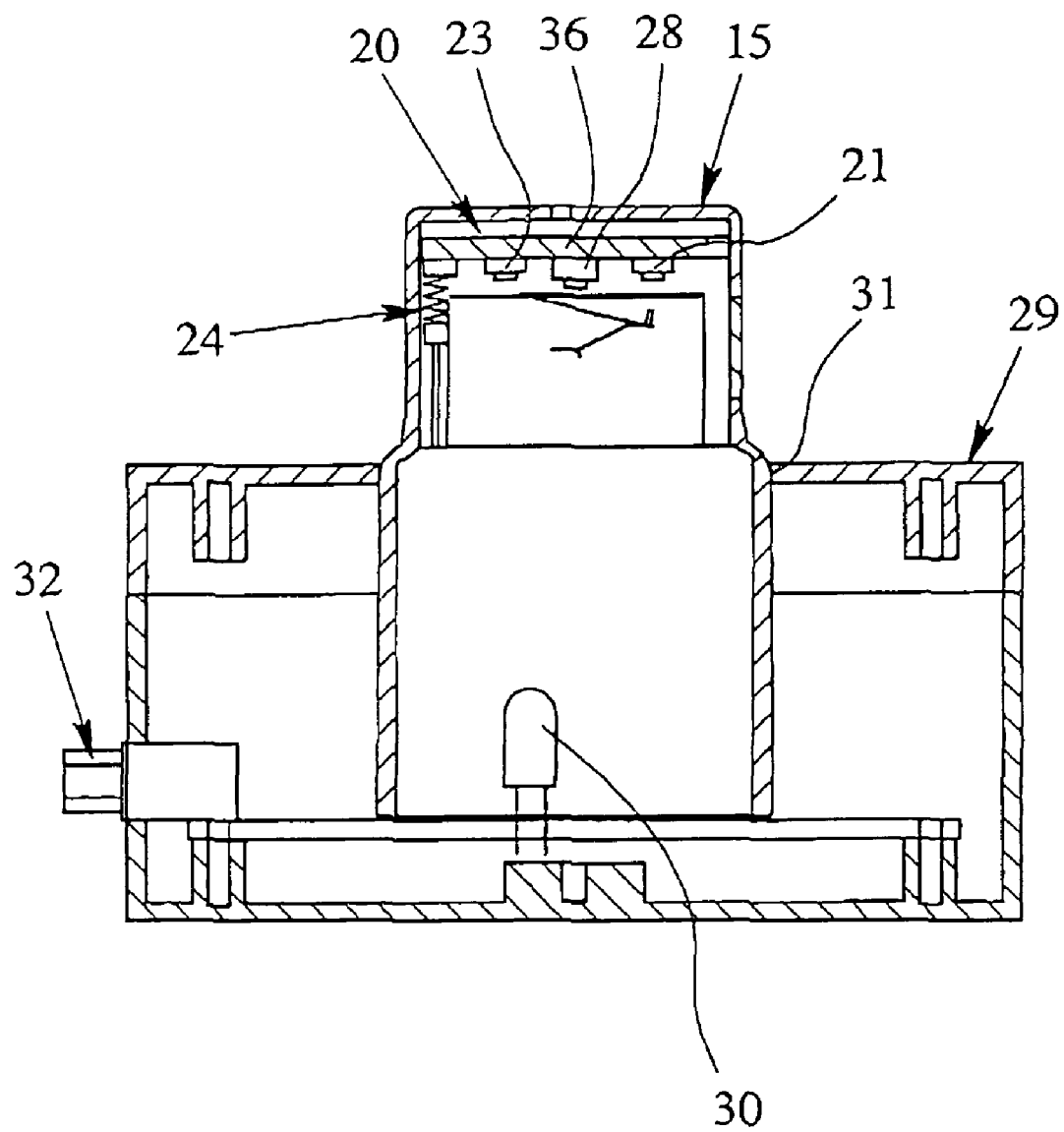
FIG. 5 is a diagrammatic representation of a connecting device for the monitoring device.

The construction and mode of operation of a proposed nebulizer 1 with a modified monitoring device 20 will now be described in more detail, referring to the sectional view in FIG. 3 and the block circuit diagram in FIG. 4, and otherwise the remarks relating to FIGS. 1 and 2 apply.

The monitoring device 20 is preferably incorporated in a detachable, and preferably, exchangeable housing part of the nebulizer 1, particularly in the actuating member 15 of the nebulizer 1. The monitoring device 20 is preferably mounted, more particularly cast, in the region of the axial end of the nebulizer 1 or of the actuating member 15.

When the container 3 is inserted, the monitoring device 20 is preferably arranged adjacent to the container base 18 of the container 3 and/or on an extension of the direction of movement or travel of the container 3.

The monitoring device 20 detects, as the actual dispensing of fluid 2, preferably, movements or strokes of the container 3, preferably by mechanical, optical, electrical, inductive, capacitive, and/or otherwise contactless means. In particular, the monitoring device 20, according to the embodiment shown, comprises a microswitch 21 or other switch, e.g., a proximity switch, inductive switch, capacitive switch, or reed contact, or a suitable sensor.

The microswitch 21 specifically provided here can be operated by a projection 22 of the spring 17. In particular, in its lower end position, i.e., with the nebulizer 1 or pressure generator 5 under tension, the container 3 depresses the spring 17 so that the projection 22 actuates the microswitch 21.

In the embodiment shown, the movements or strokes of the container 3 extend in an axial or linear manner. However, the monitoring device 20 can also or alternatively detect a non-linear or non-axial movement of the container 3 in a different construction of nebulizer 1 and/or a movement of some other part of the nebulizer 1, particularly when it is actuated. For example, the monitoring device 20 may alternatively or additionally detect actuation of the nebulizer 1 or the actual dispensing of fluid 2 by measuring the impedance of the spring 17, which varies as a function of the tensioning position.

The monitoring device 20 preferably detects, when the container 3 reaches the end position in the tensioned state and/or when it leaves this position during the nebulizing process, as an actuation of the nebulizer 1 that is counted. In particular, the monitoring device 20 comprises a control unit 23, preferably a microcontroller or the like, for carrying out the above mentioned counting and/or other functions of the monitoring device 20. The other components of the monitoring device 20 are connected to the control unit 23.

Alternatively or additionally, the monitoring device 20 can also detect movements of the container 3 or some other part of the nebulizer 1, such as the spring 17 or holder 6, and, in particular, evaluate them. Preferably, the position, speed, the associated parameters, and, especially, a distance/time curve, or the like, are detected and evaluated.

In addition, the monitoring device 20, when counting, also detects the time of actuation, which will be discussed in more detail hereinafter.

The strokes of the container 3 thus constitute a numerical value for the number of actuations of the nebulizer 1 and hence for the quantity of fluid 2 dispensed. The numerical value also indicates the fill level of the fluid 2.

Preferably, the numerical value of the actuations of the nebulizer 1 can be manually or automatically reset, particularly when changing the container 3; the number of actuations that has occurred and/or the number of possible actuations with the current container 3 being capable of being displayed and/or stored as desired. Preferably, the resetting of the numerical value takes place automatically after the fitting or pushing on of the actuating member 15, the fitting or putting on of the actuating member 15 preferably being detectable by the monitoring device 20 by means of a contact switch 24 or the like.

In the embodiment shown, the contact switch 24 can be initiated or actuated by means of a spring-loaded contact pin, the contact pin being pressed down or inwards against spring force by the inner part 14 when the actuating member 15 is fitted on. In addition to the automatic resetting of the numerical value, this embodiment has the further advantage that once the nebulizer 1 has been put together it is impossible for the contact switch 24 to be (re-)actuated and the numerical value thereby reset. This results in simple operation of the nebulizer 1 that is not susceptible to operating errors.

The contact switch 24 may additionally or alternatively serve to switch on or activate the monitoring device 20, particularly by detecting the assembly of the nebulizer 1 for the first time.

Alternatively or in addition to the contact switch 24, some other switch, such as an inductive switch, capacitive switch, reed contact, proximity switch, or the like, or any other suitable sensor, may be used.

According to an alternative embodiment, the nebulizer 1 is preferably constructed so that it can only be initiated or actuated when the monitoring device 20 is installed or added on and/or when the monitoring device 20 is switched on. This can be achieved by a suitable mechanical and/or electrical connection or coupling of the nebulizer 1 to the monitoring device 20 or optionally to the housing part or actuating member 15 containing the monitoring device 20.

In particular, the nebulizer 1 is prevented from being actuated if the monitoring device 20 is not switched on, if there is no monitoring device 20, if there is no actuating member 15, and/or if there is no container 3.

The monitoring device 20 preferably has, in particular, an optical indicator device 25, which may be, as in the embodiment shown, a display or the like, particularly for indicating the status of the monitoring device 20, the time that has elapsed since the last actuation of the nebulizer 1, the time remaining until the next actuation of the nebulizer 1, the number of actuations of the nebulizer 1 that have already occurred, the number of actuations of the nebulizer 1 that are still possible, the number of actuations of the nebulizer 1 that still have to be carried out (e.g., when inserting a new container 3), indicating whether the container has been changed or has to be changed, the fill level of fluid, identification of the container, and/or designation of the fluid. This provides optimum information and possible guidance for the user. Thus the handling of the nebulizer 1 is made easier and greater operational safety is provided.

The monitoring device 20 preferably has an acoustic indicator device 26, particularly a peso electric signal transmitter or the like, particularly for emitting a reminder signal for reminding the user that actuation of the nebulizer 1 is due and/or for indicating an ongoing and/or completed nebulizing process.

For example, by emitting an audible signal that lasts throughout the atomizing process, the monitoring device 20 can tell the user that nebulization has occurred and the user should inhale the aerosol formed accordingly. Preferably, the audible signal does not end as the nebulizing process ends, but only after a period extending beyond that to ensure that the user has inhaled all the aerosol produced. In view of the comparatively accurate period of about one to two seconds for the nebulizing process, the total duration of the audible signal may be laid down irrespective of the actual atomising process by a preferably predetermined time of, for example, three to four seconds, or about 10 to 15 seconds, if allowance is made for a desirable period of holding ones breathe after inhaling. The monitoring device 20 then emits the audible signal after the initiation of the nebulizing process by actuating the locking element 8, i.e., starting with the detection of the stroke of the container 3 in the direction of nebulizing by means of the microswitch 21.

Alternatively or in addition to the above mentioned audible signal that is emitted continuously or repeatedly during the actual nebulizing process or the nebulizing process to be displayed, the monitoring device 20 may also emit an end signal to indicate the end of the atomising process, e.g., after the predetermined time has elapsed.

In addition or alternatively, a user may be informed, by means of the acoustic indicator device 26, possibly with another signal, of the actual duration of inhaling and/or whether the inhaling was powerful enough and/or whether the inhalation was not powerful enough or did not last long enough.

Preferably, the acoustic indicator device 26 generates a sound signal that may if necessary emerge through an opening provided in the actuating member 15.

Additionally or alternatively, the acoustic indicator device 26 may cause vibration of the actuating member 15 or nebulizer 1 as a signal, i.e., it may emit a vibrating signal or a signal which is otherwise tactile.

The monitoring device 20 comprises an energy store, particularly a battery 27 or, optionally, an accumulator. The energy store is preferably only connected once the monitoring device 20 has been switched on, to allow a long shelf life with minimum loss of energy.

Preferably, the energy store or battery 27 has a capacity such that the monitoring device will remain operational for at least one year, preferably at least two years, and, in particular, at least five years after being switched on.

The monitoring device 20 also comprises an interface 28, which is preferably a light emitting diode, that preferably operates only optically, and that allows the monitoring device 20 in particular to be switched on, programmed, set, reset, and/or interrogated. That is, the monitoring device comprises a purely optical interface for switching on, initializing, programming, setting, resetting, and interrogating the monitoring device.

In order to communicate with the monitoring device 20 via the interface 28, a connecting device 29, shown, by way of example, in FIG. 5, is preferably provided. In particular, the monitoring device 20 is connectable to the connecting device 29 through the interface 28—optionally only after the monitoring device 20, together with the housing or actuating member 15, has been disconnected from the nebulizer 1. Preferably, the connecting device 29 comprises a light emitting diode 30 or the like for preferably optical communication or data transmission with the monitoring device 20.

In order to connect it up, the monitoring device 20 or actuating member 15 is adapted to be inserted in a suitable recess 31 in the connecting device 29, in particular, and/or the connecting device 29 can be at least partially inserted in the actuating member 15.

The connecting device 29 is preferably connectable to a computer or the like, e.g., through a connection 32. Accordingly, the monitoring device 20 is very easy to initiate, switch on, program, reset, interrogate, and the like. Data stored by the monitoring device 20 is accordingly easy to call up, display, and optionally evaluate. This is particularly advantageous for clinical trials and/or the monitoring of a patient by a doctor.

Alternatively or in addition, the connecting device 29 may also be suitable for use independently of a computer or the like.

If necessary, the connecting device 29 may also have its own display and/or a keyboard or other input device for switching on, programming, setting up, resetting, and/or interrogating the monitoring device 20. In particular, various parameters or the like can then be displayed and, in this case, the optical display device 25 and/or an input device 35 of the monitoring device 20 may be omitted if desired.

Instead of the battery 27, an accumulator may be used if desired. This can be charged up, for example, through an electrical connection or, possibly, inductively, especially at the same time as it is connected to the connecting device 29 and/or through a solar cell of the monitoring device 20.

The monitoring 20 is preferably constructed so that it is only switched on when first fitted together with the nebulizer 1, when the container 3 is first inserted, when the pressure generator 5 is first tensioned or actuated, and/or when it is initiated through the interface 28. This is advantageous in terms of a long shelf life.

Preferably, the monitoring device 20 cannot be switched off once it has been switched on. This ensures the desired continuous monitoring.

The monitoring device 20 preferably comprises a timer 33 and a memory 34, particularly so that the number and times of actuation of the nebulizer 1 or the dispensing of fluid 2 can be detected and stored, and/or so that repeated actuation of the nebulizer 1 within a given minimum period is preventable, and/or so that once a predetermined maximum time has elapsed the reminder signal mentioned previously for repeated actuation of the nebulizer 1 can be emitted.

When the number and times of the actuations or dispensing of fluid 2 are recorded continuously in the memory 34, it is possible, by interrogating the monitoring device 20, i.e., by reading the memory 34, to check and monitor when and to what extent the nebulizer 1 has been used or fluid 2 has been dispensed. The monitoring option is beneficial for the user for self-monitoring and/or for monitoring by the treating doctor and/or for clinical trials, particularly to check that the prescribed doses of fluid 2 are being taken.

If repeated actuation of the nebulizer 1 within a given minimum period is preventable, overdosing can be prevented.

The memory 34 preferably has an EPROM or EEPROM, while in the latter case electrical resetting is possible.

The memory 34 or its contents can preferably not be erased or altered at least by the user or patient.

Preferably, the timer 33 does not constitute an absolute time base; rather, it is a (simple) counter that only measures or provides relative time. This results in a particularly simple and inexpensive structure.

The absolute start of the resolute time measurement by the timer 33 is preferably laid down on initiating or first switching on the monitoring device 20 and is stored, in particular, in the memory 34 or by some other device, such as a computer for initiating the monitoring device 20.

Alternatively or additionally, the absolute end of the relative time measurement by the timer 33 can easily be laid down by interrogating the monitoring device 20 by comparison with an absolute time base. Thus, the absolute times of the actuations of the nebulizer 1 detected by the monitoring device 20 and stored in the memory 34 can be laid down or determined.

According to a preferred alternative embodiment, the nebulizer 1 and/or the monitoring device 20 is or are constructed so that the container 3 uses, and/or its fill level, and/or its fluid 2 can be preferably, automatically identified by the monitoring device 20 and the identification of the container can, in particular, be stored and/or indicated or displayed. In this way, it is possible to tell which container 3, and hence which fluid 2, has been used.

For example, the monitoring device 20 or the nebulizer 1 may comprise a bar code reader or other means for interrogating identification or coding, such as a bar code, on the container 3. Thus, it is possible to tell whether the wrong container 3, or a container 3 containing the wrong fluid 2, the wrong amount of fluid, and/or the wrong concentration of active substance in the fluid 2, has been used. Depending on the programming or setting of the monitoring device 20, it is then possible to block actuation of the nebulizer 1.

The monitoring device 20 preferably comprises an identifier, capable of being interrogated, for identifying the monitoring device 20, the nebulizer 1, and/or a user.

The monitoring device 20 preferably comprises, alternatively or additionally to the interface 28, a manually actuated input device 35, particularly a key, keyboard, or the like. Preferably, the monitoring device 20 can be switched on, programmed, set, reset, and/or interrogated using the input device 35. For example, using the input device 35, it is possible to input the minimum time, maximum time, and/or number of doses, e.g., the number of actuations per use and the number of uses per day.

All or at least most of the components of the monitoring device 20 are preferably mounted on a printed circuit board 36 and/or attached thereto. In particular, the monitoring device 20 forms an assembly that is inserted, preferably cast, into the housing or actuating member 15 of the nebulizer 1.

Figure 6:
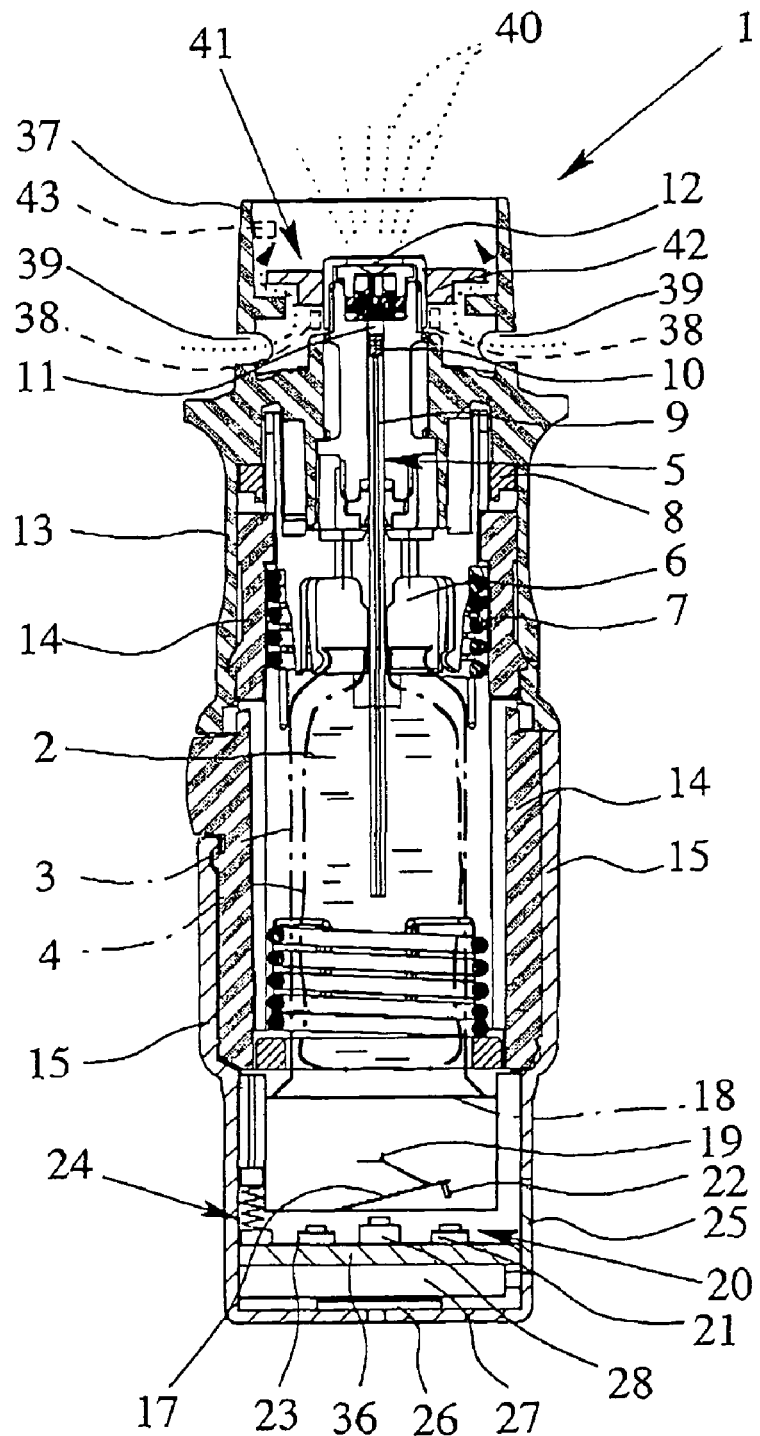
FIG. 6 is a diagrammatic section through another proposed nebulizer with a receiving sensor and a spray sensor.

According to another aspect, which may, if necessary, be implemented independently, the proposed nebulizer 1 comprises a receiving sensor 38, particularly in the region of a mouthpiece 37 or expulsion nozzle 12, for detecting an air current and/or the inhaling or nebulized fluid 2, as shown in FIG. 6.

Preferably, an air supply opening 39 is associated with the receiving sensor 38, through which an air supply can be sucked in by a user on inhalation, particularly laterally or in the region of the expulsion nozzle 12, as indicated by arrows in FIG. 6.

According to a first alternative embodiment, the receiving sensor 38 is preferably constructed directly in order to detect a corresponding air supply current, so that inhalation of the aerosol 40, as diagrammatically indicated in FIG. 6, can be detected.

Preferably, the receiving sensor 38 is able to detect the direction of an air flow through the air supply opening 39, the flow velocity, and/or the flow volume. For this purpose, the receiving sensor 38 may, for example, be constructed as a so-called "flow sensor" for directly detecting an air flow, or it may have an associated, preferably freely, pivoting flap, a flywheel that can be rotated by the air current, or the like.

According to a particularly preferred second alternative embodiment, which can also be implemented independently, if necessary, a valve 41, as diagrammatically shown in FIG. 6, and constructed, in particular, as a one-way or non-return valve, preferably having a movable valve element 42, is associated with the air supply opening or openings 39 to prevent (accidental) expulsion of the aerosol 40 through the air supply opening(s) 39. In this case the receiving sensor 38 preferably, directly detects only the opening and/or closing of the valve 41, i.e., it detects the air supply current only indirectly. This gives rise to a particularly simple and inexpensive construction, especially when the receiving sensor 38 comprises a microswitch, for example, that can be actuated by the valve element 42.

The receiving sensor 38 is preferably connected to the monitoring device 20 that evaluates the signals of the receiving sensor 38 accordingly and stores them in particular. This can be done, if necessary, without wires or even mechanically. Preferably, the receiving sensor 38 is electrically connected to the monitoring device 20 by leads and suitable contacts at the transition to the actuating member 15.

By means of the receiving sensor 38, the air supply current, and hence the actual inhaling of the aerosol 40 produced using the nebulizer 1, can be detected. Accordingly, alternatively, or in addition to detecting the movement of the container 3, the monitoring device 20 is able to count inhalation of the aerosol 40 detected by the receiving sensor 38 as an actual dispensing or uptake of the fluid 2 or (successful) actuation of the nebulizer 1 and process, display, store, etc., this numerical value in the manner described previously.

The detection of actual inhalation of the fluid 2, which is possible using the receiving sensor 38, can be evaluated by the monitoring device 20 to say whether inhalation was long enough, while the inhalation time may, if necessary, be stored and/or displayed.

According to another embodiment, the nebulizer 1 comprises, in addition or alternatively to the receiving sensor 38, a spray sensor 43 that can be used to detect whether nebulization has actually occurred. In particular, the spray sensor detects whether droplets of the nebulized fluid 2 or aerosol 40 have actually formed in the region of the mouthpiece 37. For example, the sensor makes use of the effect of light being scattered by the nebulized fluid 2 or aerosol 40 and operates as a so-called "scattered light sensor. "

The spray sensor 43 can also detect whether nebulization has actually occurred. In particular, the monitoring device 20 checks whether, on actuation of the nebulizer 1, preferably within a predetermined time window, nebulization is actually detected by means of the above mentioned sensor, and, only if actual nebulization is detected, is the actuation of the nebulizer 1 actually detected or counted as the dispensing of fluid 2 and hence as a nebulizing process.

Alternatively or in addition to detecting a movement of the container 3 or any other component, the monitoring device 20 is able to detect an air supply current by means of the receiving sensor 38 and/or can detect the production of an aerosol 40 by means of the spray sensor 43 and evaluate them, optionally only when they occur cumulatively, as an actual dispensing of fluid 2, and count them as an actuation of the nebulizer 1, and optionally store them, particularly together with the time at which they occurred.

We claim:

1. A hand-holdable nebulizer for a fluid comprising: a container containing the fluid, a manually operated, pressure generator for conveying and/or nebulizing the fluid, and a monitoring device for counting actuations of the nebulizer, wherein the monitoring device comprises a timer and a memory so that the number and times of the actuations can be detected and stored, wherein the timer measures only relative time, and wherein at least one of:

a) the absolute start of the relative time measurement is indicated by on initiating or first switching on of the monitoring device and is stored in one the memory or another device; and b) the absolute end of the relative time measurement is determined by interrogating the monitoring device and by comparison with an absolute time base wherein the monitoring device is operative for detecting the absolute times of the actuations of the nebulizer and for storing the detected absolute times in the memory.

2. A nebulizer for a fluid comprising:

a container containing the fluid, a pressure generator for at least one conveying and nebulizing the fluid, and a monitoring device for counting actuations of the nebulizer, wherein the monitoring device is mounted on a detachable outer housing part of the nebulizer, and allows the monitoring device together with the outer housing part, to be removed from the nebulizer and from the pressure generator, the outer housing part being detachable for one of inserting and replacing of the container.

3. A nebulizer for a fluid comprising:

an insertable or exchangeable container containing the fluid, a pressure generator for at least one of conveying and nebulizing of the fluid, and a monitoring device for counting actuations of the nebulizer, and and a connecting device on a housing of the nebulizer that comprises an interface for communication, via the interface, with the monitoring device, said connecting device being connectable for externally transmitting data from the monitoring device.

4. A nebulizer for a fluid comprising:

an insertable or exchangeable container containing the fluid, a mechanically driven pressure generator for at least one of conveying and nebulizing of the fluid, and a monitoring device for counting actuations of the nebulizer, and wherein at least one of the nebulizer and the monitoring device has means for interrogating identification or coding on the container and for enabling actuation of the nebulizer only when at least one of the container and fluid are identified by the interrogation as being the correct one to be used.

5. A nebulizer for a fluid comprising:

a mouthpiece, an insertable or exchangeable container containing the fluid, a pressure generator for at least one of conveying and nebulizing of the fluid, and a monitoring device for counting actuations of the nebulizer, wherein the monitoring device is adapted so that actual dispensing of fluid can be detected and counted electronically as an actuation of the nebulizer, and wherein an optical spray sensor is provided which optically detects whether droplets of the nebulized fluid or aerosol have actually formed in the region of the mouthpiece.

* * * * *